United States Patent [19]

Palinczar

[11] Patent Number: 4,710,371

[45] Date of Patent: Dec. 1, 1987

[54] WATERPROOF SUNSCREEN COMPOSITIONS

[76] Inventor: Victor Palinczar, 435 Adeline St., Trenton, N.J. 08611

[21] Appl. No.: 830,838

[22] Filed: Feb. 19, 1986

[51] Int. Cl.$^4$ .......................... A61K 7/42; A61K 7/44; A61K 9/12

[52] U.S. Cl. ........................................ 424/47; 424/59; 424/60

[58] Field of Search ............................... 424/59, 60, 47

[56] References Cited

U.S. PATENT DOCUMENTS

| | | | |
|---|---|---|---|
| 3,004,896 | 10/1961 | Heller et al. | 424/59 |
| 3,068,153 | 12/1962 | Morehouse | 424/59 |
| 3,670,074 | 6/1972 | Doner | 424/59 |
| 4,293,544 | 10/1981 | Elmi | 424/47 |
| 4,559,225 | 12/1985 | Fourman | 424/59 |

FOREIGN PATENT DOCUMENTS 2028131  3/1980  United Kingdom ................. 424/60

*Primary Examiner*—Dale R. Ore

[57] ABSTRACT

An effective aesthetic water-proof sunscreen composition which includes ultraviolet light protection to the skin includes polybutene polymers in an amount from 5% up to about 98% by weight and from about 1% to about 30% by weight of an active sunscreen agent.

The composition may optionally contain from about 0% to about 15% by weight of a surface active agent, from about 0% to about 20% by weight of water-insoluble emollients, from about 0% to about 20% by weight of suspended particulate matter, from 0% to about 85% by weight of a volatile liquid carrier, from 0% to about 15% by weight of thickening agents, from 0% to about 3% of fragrance oil, from 0% to about 85% by weight of water and from 0% to about 85% by weight liquified propellent.

21 Claims, No Drawings

WATERPROOF SUNSCREEN COMPOSITIONS

BACKGROUND OF THE INVENTION

1. Field of the Invention

This invention relates to novel sunscreen compositions which, when applied to the human skin provide protection against the harmful effects caused by ultraviolet radiation. More particularly, this invention relates to sunscreen compositions in the form of oils, lotions, creams and aerosols wherein an ultraviolet light-absorbing ingredient is placed on the skin and is provided with increased water resistant characteristics with the aid of a polymeric binder. Most particularly, this invention relates to sunscreen compositions that are water-proof and fulfill the guidelines established by the Food and Drug Administration, as listed in the Federal Register: Volume 43, Number 166.

2. Discussion of the Relevant Art

Sunscreen compositions are commonly used during outdoor activity. Many people have occupations which require them to be exposed to the sun for long periods of time. Others choose to use their free time in outdoor recreations e.g. sunbathing, playing golf, surfing, fishing, skiing and swimming. All of these activities promote perspiration or allow the body to come in contact with water. Numerous sunscreen compositions have been developed which absorb ultraviolet light in a region of 280 to 320 nanometers (2800–3200 Angstroms; referred to as the "erythemal region") to protect the human body against this radiation that produces erythema and skin cancer, whether the source be from the sun or from man made devices. These compositions also incorporate ultraviolet absorbing agents that absorb in the region between 320 and 380 nonometers (3200–3800 Angstroms) and should be resistant to removal from the skin by perspiration or water in order to broaden and prolong their effectiveness.

Numerous substantive sunscreen agents, and substantive and water-resistant sunscreen compositions are available today. Development of substantive sunscreen agents and sunscreen compositions containing these substantive agents are illustrated in U.S. Pat. No. 3,864,473 issued to Cicendelli; U.S. Pat. No. 4,004,074 issued to Gerecht; and U.S. Pat. No. 4,256,664 issued to Epstein. These compositions make use of sunscreen agents that are not approved by the FDA and their topical use in limited.

No known sunscreen agent, that achieves a degree of water-resistancy, has been approved by the Food and Drug Administration. FDA approved sunscreen agents have, however, been incorporated into compositions which upon application to the skin physically keep the sunscreen agent on the skin during perspiration or immersion in water. The majority of these compositions make use of polymeric materials that are either emulsified in the composition or carried to the skin by a vehicle in which a continuous polymeric film is cast on the skin.

The use of an acid form of a cross-linked co-polymer of ethylene-maleic anhydride composition in the form of a gel is illustrated in U.S. Pat. No. 3,821,363 issued to Black. Compositions and methods are described in U.S. Pat. No. 3,895,104 issued to Karg in which polyamide resinous material is used as a film former. The use of acrylate/acrylic acid copolymer compositions in the form of oils and emulsions are illustrated in U.S. Pat. No. 4,172,122 issued to Kubik. In U.S. Pat. No. 4,254,102 issued to Kaplan there is described the use of compositions containing hydroxyethyl-cellulose in conjunction with a surface active agent and a fatty alcohol. In U.S. Pat. No. 4,193,989 issued to Teng, there is described gel compositions of hydroxypropyl cellulose acetate as the film former.

Known compositions that make use of polymers to form a continuous polymeric film in which the active sunscreen agent is homogeneously dispersed throughout the matrix of the film have numerous disadvantages. Aqueous based compositions in which the polymer is usually emulsified have long drying rates on the skin, foam on the skin during application and during the drying cycle leave the skin feeling tacky. These compositions, if not fully dried, also have a tendency to allow particulate matter, such as beach sand, to adhere to the skin. Furthermore, the water-resistant properties of these aqueous based compositions are decreased if they are not fully dried before perspiration or entry into water. The formation of a continuous protective film on the skn is prevented by compositions which make use of solvent systems because they cannot tolerate large amount of oil and other emollients. Without the use of emollients in compositions containing alcohols, the skin may become dry and irritated. Generally these compositions are also formulated in thin solutions with low viscosities which make them difficult to apply to the skin in an even manner.

Compositions, which make use of an ethylcellulose polymer in combination with ethanol as a solvent and are effective in resisting water wash off, are products currently marketed by Carter-Wallace, Inc., New York, N.Y. under the trade names of BLOCK OUT and SEA & SKI. These compositions, however, are low in viscosity, contain high levels of silicone fluids and are costly to produce. They are also difficult to apply to the skin evenly thus permitting spot burning to occur, which may result in extreme pain and blistering of the skin. This effect is more pronounced with individuals having fair complexions and who normally use sunscreen products having high SPF (Sun Protection Factor) values. Water-resistant compositions described heretofore that contain high levels of solvents that are currently being marketed in addition to being difficult to apply to the skin evenly, lack the ability to be made in a range of viscosities, thus limiting the formulator in his selection of ingredients to be used in a composition and separate systems must be developed to fulfill the needs of the consumer.

Furthermore, compositions having high solvent concentrations lack the ability to homogeneously suspend particulate matter throughout the matrix of the composition thereby preventing the use of insoluble solid ingredients which have a tendency to prevent ultraviolet radiation from being absorbed by the skin.

The present invention overcomes the shortcomings of known water-resistant sunscreen compositions by incorporating ingredients that resist removal of the active sunscreen agent by perspiration and water when applied to the skin. The present invention, in combination with ingredients that allow the composition to be solvent free in nature with a range of viscosities, have the ability to suspend insoluble particulate matter, that can be applied to the skin evenly and easily, that protect the skin from the harmful effects of the sun's radiation, and that dry quickly without leaving the skin feeling tacky. There is a need for such a product for both health and cosmetic reasons. Ingredients may be available which exhibit one or more of these desired attributes but the combination of these attributes, for use in preparing water-proof sunscreen systems has not been demonstrated. Ingredients fulfilling these requirements, which have not been used previous to this invention in water-proof solvent free sunscreen compositions are the combination of active sunscreen agents and polybutene polymers.

SUMMARY OF INVENTION

This invention relates to very effective, highly aesthetic water-proof sunscreen composition in the form of oils, lotions, creams and aerosols which provide ultraviolet light protection to the skin comprising polybutene in an amount of up to 98% by weight and from about 1% to about 30% by weight of an active sunscreen agent.

The compositions may optionally contain from about 0% to about 15% by weight of a surface active agent, from about 0% to about 20% by weight of water-insoluble emollients, from about 0% to about 20% by weight of suspended particulate matter, from 0% to about 85% by weight of a volatile liquid carrier, from 0% to about 15.0% by weight of thickening agents, from 0% to about 3% of fragrance oil, from 0% to about 85% by weight of water and from 0% to about 85% by weight of liquified propellant.

DETAILED DESCRIPTION OF THE INVENTION

It has been discovered that highly effective, non-irritating cosmetically aesthetic water-proof compositions in the form of oils, lotions, creams and aerosols containing a polymer such as polybutene and an active sunscreen agent are prepared by combining the polybutene and the active sunscreen agent together and mixing until a complete solution is formed. Optional ingredients may be combined with the mixture to prepare different forms of end products by numerous methods known by those skilled in the arts. Methods for preparing different forms of products are fully described and illustrated hereinafter.

It has also been discovered that the polybutene polymers, although highly hydrophobic, and unlike alkane polymers and liquids having similar molecular weights, are compatible with numerous active sunscreen agents, such as benzophones, which normally are incompatible with such highly hydrophobic compounds. Until the present discovery such combinations have not yet been disclosed.

It has further been discovered that the polybutene polymers, unlike alkane polymers and liquids having similar molecular weights, are less cohesive in nature and are inherently adhesive to skin resulting in highly substansive sunscreen compositions.

It has still further been discovered that the polybutene polymers unlike alkane polymers and liquids having similar molecular weights are less oily and greasy when applied to the skin resulting in highly aesthetic sunscreen compositions.

It has additionally been discovered that the compositions may additionally contain water-insoluble emollients for the purpose of preventing the skin from drying. The water-insoluble emollients also add body to the composition and decrease the tackiness of the composition during dryout.

It has also been discovered that the composition may additionally contain volatile liquid organic carriers which serve to control the amount of product applied to the skin allowing the formation of a thin, evenly formed, continuous polymer film.

It has still further been discovered that the composition may additionally contain water in combination with a surface active agents, which serve to form emulsion in the form of lotions and creams.

It has additionally been discovered that the composition may additionally contain liquified propellants which serve to propel the composition from a conventional aerosol container.

It has still additionally been discovered that the composition may additionally contain suspended particulate matter which serve as an auxiliary means to reflect and/or filter ultraviolet radiation. The suspended particulate matter may also serve as a cosmetic additive to make the composition more glamorous in the container and/or on the skin. It has still additionally been discovered that the composition may additionally contain thickening agents which serve to increase the viscosity of composition allowing for the composition to be made in a variety of viscosities ranging from thin lotions to thick creams. The composition may also contain fragrance oil. These ingredients are more specifically described below.

While not wishing to be limited by any theory of the mechanism of the activity of the invention, it is believed that the use of polybutene polymers is very important in maintaining both the degree of water resistancy and the ability to be compatible with a variety of ingredients to form a continuous film of the compositions mentioned herein on the skin.

When the water-proof composition of the present invention is applied to the skin in any of the various forms mentioned hereintofore, any constituent of the compositions, which is volatile, evaporates from the skin leaving a water-insoluble flexible film consisting primarily of polybutene polymer and active sunscreen agents. The water-insoluble film also helps prevent the loss of the active sunscreen agents by physical abrasion and is unaffected by bodily salts expelled from the body during perspiration. It is also believed that the polybutene film allows perspiration to pass through the continuous film in the vapor state, thereby leaving the film intact and continuous. It is further believed that the polybutene polymer has an inherent propensity to adhere to the skin and in addition to containing the active sunscreen agent within its media, immobilizes the active sunscreen agent, preventing migration from the matrix of the film keeping the active sunscreen agent on the surface of the skin, thereby decreasing percutaneous absorption through the skin and diffusion on the surface of the skin of the active sunscreen agent. It is therefore believed that the combination of these actions cause these compositions to be effective for long periods of time and to resist removal by water and perspiration.

THE POLYMERIC FILM FORMER

Polybutene polymers, such as the Indopols manufactured by (Amoco Chemicals Corp., Chicago, Ill.) are Isobutylene Butene copolymers having an average molecular weight from about 200 to about 2500, a pour point of about $-65$ degrees to about 20 degrees C., a specific gravity of about 0.910 or less at 15.6 degrees C., a viscosity of 5000 centistokes or less at 100 degrees C., and a water solubility of less than 0.0015% at 25 degrees C.

Preferred polybutene polymers used in this invention have a molecular weight from about 280 to about 750 and a pour point range from about −51 degrees C. to about −15 degrees C. The present composition may contain up to 98% of polybutene polymers. The preferred amount of polybutene polymer is from about 30% to about 70% and most preferably from about 40% to about 60%. Amounts of less than 30% are also acceptable if used in combination with water-insoluble liquid emollients, volatile liquid carriers such as Isopropanol or volatile silicone fluids. Compositions containing levels of 5% by weight of polybutene polymer having an average molecular weight from 460 to about 2500 and a pour point range from about −35 degrees C. to about 18 degrees C. when used in combination with water or liquified propellants, such as Isobutane and Propane, provide adequate application to the skin with acceptable drying time and overall aesthetics.

It will be understood that if one replaces any portion of the polybutene polymer, with one ingredient or a mixture of any ingredients mentioned in this invention that do not have degrees of hydrophobicity and adhesion to the skin similar to that of the polybutene polymers, compositions prepared with these ingredients or a mixture of these ingredients, will have their drying rates, water resistancy, sunscreen efficacy and overall cosmetic aesthetics reduced. However, so long as the final compositions have at least 5% polybutene polymers by weight, these compositions will still be more water resistant and effective than compositions without the use of the polybutene polymers. It will be further understood that the polybutene polymers provide excellent compatibility with an array of cosmetically acceptable ingredients, and any ingredient combination may be made without departing from this spirit and scope of this invention.

THE ACTIVE SUNSCREEN AGENT

Any active sunscreen agent, capable of absorbing the harmful effects of ultraviolet radiation which is non-irritating, non-toxic and is compatible with the ingredients used in the composition and which when applied to the skin are homogeneously dispersed throughout the film formed, by the ethylcellulose polymer, can be used. Active sunscreen agents that meet these criteria are: PABA (para-aminobenzoic acid); Cinoxate (2-ethoxyethyl p-methoxycinnamate); diethanolamine p-methoxycinnamate; digalloyl trioleate; Dioxybenzone (2,2'-dihydroxy-4-methoxybenzophenone); ethyl 4 [bis(-hydroxypropyl)] aminobenzoate; 2-ethylhexyl 2-cyano-3, 3-diphenylacrylate; ethylhexyl p-methoxycinnamate; 2-ethylhexyl salicylate; glyceryl aminobenzoate; Homosalate (3,3,5-trimethylcyclohexyl salicylate); menthyl anthranilate (menthyl o-aminobenzoate); Oxybenzone (2-hydroxy-4-methoxybenzophenone); Padimate A (amyl p-dimethylaminobenzoate); Padimate O (octyl p-dimethylaminobenzoate); and triethanolamine salicylate.

The present invention may contain from about 1% to about 30% by weight of these active sunscreen agents or a mixture thereof. The preferred total amount of the active sunscreen agent is dependent upon the SPF value (sun protection factor) desired to be obtained. The preferred sunscreen agents in the present invention are Padimate O in amounts from 2% to about 10% by weight; Padimate A in amounts from 1% to about 8% by weight; 2-ethylhexyl salicylate in amounts from 3% to about 8% by weight; ethylhexyl p-methoxycinnamate in amounts from 2% to about 8% by weight; Dioxybenzone from 1% to about 5% by weight and Oxybenzone from 1% to about 7% by weight.

THE SUSPENDED PARTICULATE MATTER

The present composition may additionally contain, as an optional ingredient, from about 0% to about 20% by weight of suspended particulate solid matter which is insoluble in the ingredients used in the composition. From these solids a group of solids have been selected which are inert in the composition, having a low degree of irritation and toxicity, that are generally considered safe for topical use, that provide for a cosmetic benefit and reflect and/or absorb ultraviolet radiation. Solids that are used for cosmetic purposes are solid materials that produce a "glitter", "sparkle" or "pearlesant" effect when exposed to natural or artificial light. Preferred solids for cosmetic purposes include such solids as bismuth oxychlorid, mica and colorized acrylic polyester. The preferred solid in the present composition, for cosmetic use, is the colorized acrylic polyester. The preferred amount of solid used for cosmetic purposes in the present invention is from 0.5% to about 10% by weight.

The preferred solid used in the present invention for the purpose of reflecting or absorbing ultraviolet radiation are solids such as zinc oxide, and titanium dioxide. These solids are generally used in a powder form in which the average particle size is less than 100 microns. The preferred amount of suspended particulate solid matter used in the present invention for the purpose of reflecting ultraviolet radiation is from about 5% to about 15% by weight.

THICKENING AGENTS

The present composition may also contain, as an optional ingredient, from about 0% to about 15% by weight of a thickening agent. Thickening agents, which can be used in the present invention are ingredients that have a propensity for hydrophobic compounds, that allow the formation of a laminated network of thickening agent molecules producing an increase in the viscosity of the composition, which are non-irritating, non-toxic and are compatible with the ingredients used in the composition which when applied to the skin allow the formation of a continuous polymeric film in which the active sunscreen agent is homogeneously dispersed. Examples of such thickening agents are selected from a group consisting of synthetic polymers such as polyethylene polymers sold under the Tradename of AC Polyethylene by (Allied Chemical, Morristown, N.J.); organic salts such as zinc stearate; fatty acids such as stearic, fatty alcohols such as myristyl, esters such as glycerol stearate; Natural waxes such as paraffin, carnauba, spermaceti, and microcrystalline; inorganic salts such as fumed silica,, amorphous silica, sodium magnesium silicate and colloidal magnesium aluminum silicate. The preferred thickener is zinc stearate. The preferred amount of the thickening agent is from 0.5% to about 8% by weight.

THE SURFACE ACTIVE AGENT

Surface active agents used in the present composition are defined as surface active agents that allow for the formation of emulsions preferably water-in-oil emulsion, which are viscous lotions or creams consisting of the polybutene polymer, active sunscreen agent, water and any optional ingredient used in the compositions of the present invention.

The function of the surface active agents used in the present invention which are used for the purpose of forming an emulsion is to physically unite the polybutene polymer, active sunscreen agent and water, which are not compatible under normal conditions, by decreasing the interfacial tension, and allowing the formation of hydrogen bonding in which sub-micron particles of polybutene polymer/active sunscreen agent are formed and remain suspended for long periods of time throughout the water media.

Surface active agents which can be used in the present invention for the purpose of forming viscous lotion or cream emulsions are those which are non-irritating, non-toxic and are compatible with the ingredients used in the composition which when applied to the skin allow the formation of a continuous polymeric film in which the active sunscreen agent is homogeneously dispersed which are selected from a group consisting of anionic surfactants such as alkanolamides, and alkyl ether sulfates; nonionic surfactants such as ethers derived from the condensation of fatty acids and ethylene oxide; and of soaps of fatty acids such as ammonium myristate, triethanolamine stearate and potassium oleate.

The preferred surface active agents are soaps of fatty acids and those which are nonionic in nature which have a tendency to form water-in-oil emulsions. To those skilled in the arts, there are numerous known varieties of nonionic surface active agents which will form such emulsions. Since the overall hydrophile-lipophile balance of an emulsion is the prime factor in emulsion formation, which includes all of the ingredients in the composition and most specifically those ingredients which are to emulsified, applicant wishes not to be limited to any specified surface active agents. It will be further understood that the surface active agents provide excellent compatibility with an array of cosmetically acceptable ingredients, and any combination may be made without departing from the spirit and scope of this invention. The present invention may optionally contain from about 0% to about 15% by weight of the surface active agents described heretofore. The preferred amount of surface active agent used in the present composition for the purpose of forming an emulsion is from about 2% to about 6% by weight.

THE PROPELLANT

The present composition may also contain, as an optional ingredient, from about 0% to about 85% by weight of a liquified propellant.

Any liquified propellant, capable of producing a sufficient vapor pressure for expelling the composition from a conventional aerosol container which, is non-irritating, non-toxic and is compatible with the ingredients used in the composition and when applied to the skin allows the formation of a continuous polymer film in which the active sunscreen agent is homogeneously dispersed, can be used. Propellants that meet these criteria are: butane; isobutane; propane; dimethyl ether; dichlorodifluoromethane; tetrafluoromethane; dichlorotetrafluoroethane; chlorodifluoromethane; chlorodifluoroethane; and fifluoroethane. The preferred propellants of the present invention are isobutane and propane. The preferred amount of liquified propellant is from about 20% to about 50%.

VOLATILE LIQUID CARRIER

The present composition may also contain, as an optional ingredient, from about 0% to about 85% by weight of a volatile liquid carrier. Such liquids are in the liquid state at room temperature (about 22 degrees C.) and evaporate completely from the skin within thirty minutes after applying the composition of the present invention onto the body. From these liquids a group of liquids have been selected which are organic in nature having a low degree of irritation and toxicity, that are generally considered safe for topical use, that provide for a controlled deposition on the skin of the polybutene polymers used in the present composition, that allow for the formation of a continuous polymeric film of polybutene polymer and active sunscreen agents are hereinafter referred to as volatile liquid carriers of the present composition. Preferred volatile liquid carriers include but are not limited to cyclic dimethylpolysiloxanes (volatile silicones), trichlorofluoromethane, isopropanol and $C_{10}$-$C_{16}$ isoparaffins. The most preferred volatile liquid carriers are $C_{12}$-$C_{14}$ isoparaffins and volatile silicones. The preferred amount of the volatile liquid carrier is from about 35% to about 60% by weight.

THE WATER-INSOLUBLE EMOLLIENT

The present composition may additionally contain, as an optional ingredient, from about 0% to about 20% by weight of water-insoluble materials having a water solubility of less than about 1% at 25 degrees C. From these materials a group of compounds have been selected which are organic in nature having a low degree of irritation and toxicity, that are generally considered safe for topical use, that provide a softening or soothing effect on surface skin tissue are hereinafter referred to as the water-insoluble emollients in the present composition. Preferred water-insoluble emollients include fatty acids such as oleic and stearic; fatty alcohols such as cetyl, and hexadecyl (ENJAY); esters such as diisopropyl adipate and isononyl iso-nonanoate; alkanes such as mineral oil; silicones; such as dimethyl polysiloxane and ethers such as polyoxpropylene butyl ethers and polyoxypropylene cetyl ethers. The most preferred water-insoluble emollients are: diisopropyl adipate, dimethylpolysiloxane 50 cst. and polyoxypropylene (14) butyl ether. The preferred amount of water-insoluble emollient is from about 2% to about 15% by weight, and most preferrably from about 4% to about 10%.

The water-insoluble emollient can be used to control the rate of evaporation of the composition. In addition to providing emolliency, they also aid in controlling the amount of product deposited on the skin and the tackiness of the composition. One skilled in the art will easily be able to adjust the cosmetic aesthetics and physical characteristics of the composition by combining various suitable water-insoluble emollients in the proper proportions with the ingredients of the composition mentioned hereintofore.

The water-proof compositions of the present invention may be made in a variety of ways to those skilled in the art. One method for preparing compositions in the form of water-proof oils is to dissolve the active sunscreen agent in the polybutene polymer with agitation in a suitable vessel until a complete solution is formed. Optional ingredients such as volatile liquid carriers and water-insoluble emollients may then be added and mixed until a complete solution is formed. The composition may then be placed in a suitable container.

A similar preparation may be employed for preparing anhydrous water-proof compositions in the form of lotions and creams. In this procedure the active sunscreen agent, polybutene and any optional ingredient with the exception of particulate suspended matter, are combined together in a suitable vessel with mixing and heated to about 75 degrees C. at which time a thickening agent such as zinc stearate or polyethylene polymer is added and mixed until dissolved. The mixture is allowed to cool, which results in the formation of viscous lotion or a thick cream product. During the cooling process fragrance and the particulate matter can be added to the composition before thickening occurs.

Another procedure for preparing anhydrous waterproof compositions, in the form of aerosol sprays, is to dissolve the active sunscreen agent in the polybutene polymer and combine the desired optional ingredients with agitation until a complete solution is formed. The mixture is then placed in a conventional aerosol container, affixed with a standard aerosol valve and pressurized with liquified propellant.

In another procedure, where it is desirable to prepare a water-proof composition in the forms of aqueous lotions and creams by emulsion formation, the polybutene polymer, active sunscreen agent, surface active agent and any water-insoluble optional ingredient, with the exception of suspended particulate matter, are combined in a suitable vessel and heated to about 75 degrees C. This portion of the composition is referred to as the oil phase. To a separate vessel, water and any water-soluble ingredient is mixed until a complete solution is formed and is also heated to 75 degrees C. This portion of the composition is referred to as the water phase. When both phases are at 75 degrees C., the water phase is added to the oil phase with agitation. The composition is cooled to a temperature between 40-65 degrees C. at which time the suspended particulate matter and fragrance may be added if it is desired. The composition is further cooled to room temperature and placed in a suitable container.

To illustrate compositions prepared using the foregoing procedures the following examples are provided:

OIL COMPOSITIONS

EXAMPLE 1

| INGREDIENTS | PERCENT BY WEIGHT |
|---|---|
| *Indopol "L-14" | 92.0 |
| Padimate O | 8.0 |
| | 100.0 |

*Indopol "L-14" is the Tradename for a polybutene polymer having an Avg. Mol. Wt. 320 and a Pour Point Range −54 to −48 degrees C. marketed by AMOCO CHEMICALS CORPORATION, Chicago Illinois 60601

EXAMPLE 2

| INGREDIENTS | PERCENT BY WEIGHT |
|---|---|
| Indopol "L-14" | 87.0 |
| Padimate O | 8.0 |
| Oxybenzone | 2.0 |
| Diisopropyl Adipate | 3.0 |
| | 100.0 |

EXAMPLE 3

| INGREDIENTS | PERCENT BY WEIGHT |
|---|---|
| Indopol "L-14" | 50.0 |
| Ethylhexyl p-Methoxycinnamate | 7.5 |
| 2-Ethylhexyl Salicylate | 4.5 |
| $C_{12}$–$C_{14}$ Isoparaffins | 36.0 |
| *Indopol H-1900 | 3.0 |
| | 100.0 |

*Indopol H-1900 is the Tradename for a polybutene polymer having an Avg. Mol. Wt. 18,700 and a Pour Point Range 15 to 23 Degrees C. marketed by AMOCO CHEMICALS CORP.

EXAMPLE 4

| INGREDIENTS | PERCENT BY WEIGHT |
|---|---|
| *Indopol "L-100" | 10.0 |
| Padimate O | 8.0 |
| Cyclic Dimethylpolysiloxane | 52.0 |
| Isopropanol | 30.0 |
| | 100.0 |

*Indopol "L-100" is the Tradename for a polybutene polymer having an Avg. Mol. Wt. 460 and a Pour Point Range −38 to −32 Degrees C. marketed by AMOCO CHEMICALS CORP.

LOTION COMPOSITIONS

EXAMPLE 5

| INGREDIENTS | PERCENT BY WEIGHT |
|---|---|
| Indopol "L-14" | 32.5 |
| Padimate O | 8.0 |
| Zinc Stearate | 7.5 |
| Cyclic Dimethylpolysiloxane | 51.0 |
| Glitter | 1.0 |
| | 100.0 |

EXAMPLE 6

| INGREDIENTS | PERCENT BY WEIGHT |
|---|---|
| Indopol "L-14" | 47.0 |
| Padimate O | 8.0 |
| Oleic Acid | 4.0 |
| Triethanolamine | 1.0 |
| Water | 40.0 |
| | 100.0 |

EXAMPLE 7

| INGREDIENTS | PERCENT BY WEIGHT |
|---|---|
| Indopol "L-14" | 68.5 |
| Padimate O | 5.5 |
| Polyoxyethylene (4) lauryl ether | 5.5 |
| Water | 20.5 |
| | 100.0 |

CREAM COMPOSITIONS

EXAMPLE 8

| INGREDIENTS | PERCENT BY WEIGHT |
|---|---|
| Indopol "L-14" | 30.0 |
| Padimate O | 8.0 |
| Zinc Stearate | 11.0 |

-continued

| INGREDIENTS | PERCENT BY WEIGHT |
|---|---|
| Cyclic Dimethypolysiloxane | 50.0 |
| Fragrance | 1.0 |
| | 100.0 |

EXAMPLE 9

| INGREDIENTS | PERCENT BY WEIGHT |
|---|---|
| Indopol "L-14" | 59.0 |
| Indopol "H-1900" | 5.0 |
| Padimate O | 8.0 |
| Oxybenzone | 2.0 |
| AC polyethylene 6* | 11.0 |
| Zinc Oxide | 15.0 |
| | 100.0 |

*AC Polyethylene 6 is the Tradename for a polyethylene homopolymer marketed by ALLIED CHEMICAL, Morristown, New Jersey.

EXAMPLE 10

| INGREDIENTS | PERCENT BY WEIGHT |
|---|---|
| Indopol "L-100" | 30.0 |
| Stearic Acid | 5.0 |
| Ethylhexyl p-Methoxycinnamate | 8.0 |
| Triethanolamine | 1.5 |
| Cetyl Alcohol | 1.0 |
| Propylene Glycol | 1.0 |
| Water | 53.5 |
| | 100.0 |

AEROSOL SPRAY COMPOSITIONS

EXAMPLE 11

| INGREDIENTS | PERCENT BY WEIGHT |
|---|---|
| Indopol "L-14" | 42.0 |
| Padimate O | 8.0 |
| Isobutane | 25.0 |
| Propane | 5.0 |
| Isopropanol | 20.0 |
| | 100.0 |

EXAMPLE 12

| INGREDIENTS | PERCENT BY WEIGHT |
|---|---|
| Indopol "L-100" | 30.0 |
| Padimate O | 8.0 |
| Ethylhexyl p-Methoxycinnamate | 7.5 |
| Cyclic Dimethypolysiloxane | 23.5 |
| Fragrance | 1.0 |
| Isobutane | 25.0 |
| Propane | 5.0 |
| | 100.0 |

EXAMPLE 13

| INGREDIENTS | PERCENT BY WEIGHT |
|---|---|
| *Indopol "H-100" | 10.0 |
| Padimate A | 6.0 |
| 2-Ethylhexyl Salicylate | 4.0 |
| Dimethylpolysiloxane 50 cst | 1.0 |
| $C_{12}$–$C_{14}$ Isoparaffin | 29.0 |
| Trichlorofluoromethane | 20.0 |

-continued

| INGREDIENTS | PERCENT BY WEIGHT |
|---|---|
| Dichlorodifluoromethane | 30.0 |
| | 100.0 |

"H-100" is the Tradename for a polybutene polymer having an Avg. Mol. Wt. 920 and a Pour Point Range −10 to −2 Degrees C. marketed by AMOCO CHEMICALS CORP.

EXAMPLE 14

| INGREDIENTS | PERCENT BY WEIGHT |
|---|---|
| Indopol "H-1900" | 5.0 |
| Padimate O | 8.0 |
| $C_{12}$–$C_{14}$ Isoparaffin | 37.0 |
| Cylcic Dimethypolysiloxane | 20.0 |
| Isobutane | 25.0 |
| Propane | 5.0 |
| | 100.0 |

The examples illustrated hereintofore were applied on the skin and allowed to dry for fifteen minutes. They were then tested using the prescribed water resistancy test method described in the Federal Register Volume 43, Number 166, and were considered to be resistant to removal from the skin by water and perspiration while maintaining their dry SPF value for periods of up to 80 minutes.

What I claim is:

1. A water-proof sunscreen composition comprising:
   A. from about 5% to about 98% by weight of isobutylene-butene copolymers having an average molecular weight from about 200 to about 2500; and
   B. from about 1.0% to about 30.0% by weight of an active ultraviolet radiation absorber.

2. A water-proof sunscreen composition according to claim 1 wherein said ultraviolet radiation absorbers are selected from the group consisting of para-aminobenzoic acid; 2-ethoxyethyl p-methoxycinnamate; diethanolamine p-methoxycinnamate; digalloyl trioleate; 2,2′ dihdroxy-4-methoxybenzophenone; ethyl 4-[bis(hydroxypropyl)] aminobenzoate; 2-ethylhexyl salicylate; glyceryl aminobenzoate; 2-ethylhexyl 2-cyano-3, 3-diphenylacrylate; ethylhexyl p-methoxycinnamate; 3,3,5-trimethylcyclohexyl salicylate; menthyl o-aminobenzoate; 2-hydroxy-4-methoxybenzophenone; amyl p-dimethylaminobenzoate; octyl p-dimethylaminobenzoate; 2-phenylbenzimidazole-5-sulfonic acid; 5-benzoyl-4-hydroxy-2 methoxybenzene sulfonic acid; triethanolamine salicylate; 4-Tert. butyl-4-methoxy-dibenzoylmethane; and Benzalphthaline.

3. A water-proof sunscreen composition specified in claim 1 which additionally comprises:
   A. from about 0% to about 20% by weight of a water-insoluble organic emollient compound having a water-solubility of less than 1% at 25 degrees C. selected from the group consisting of fatty alcohols, fatty acids, esters, ethers, alkanes, and polysiloxanes;
   B. from about 0% to about 15% by weight of a surface active agent selected from the group consisting of nonionic esters, nonionic ethers and soaps of a fatty acid and an alkali metal, ammonium and an alkanolamine;
   C. from about 0% to about 85% by weight of a volatile liquid carrier having a melting point less than 22 degrees C. which completely evaporates from the skin after thirty minutes after application to the skin selected from the group consisting of monohydric alcohols, hydrocarbons, halogenated hydrocarbons and cyclic dimethylpolysiloxanes;

D. from about 0% to about 85% by weight of water;

E. from about 0% to about 20% by weight of suspended particulate solid matter;

F. from about 0% to about 85% by weight of liquified propellants;

G. from about 0% to about 15% by weight of a thickening agent selected from the group consisting of natural waxes, synthetic polymers, inorganic salts, fatty acids, fatty alcohols, esters, and organic salts; and H. from about 0% to about 3% by weight of a fragrance oil.

4. A water-proof sunscreen composition as specified in claim 3 wherein:

A. said active ultraviolet radiation absorber is selected from the group consisting of para-aminobenzoic acid; 2-ethoxyethyl p-methoxycinnamate; diethanolamine p-methoxycinnamate; digalloyl trioleate; 2,2'-dihydroxy-4-methoxybenzophenone; ethyl 4-[bis(hydroxypropyl)] aminobenzoate; 2-ethylhexyl salicylate; glyceryl aminobenzoate; 2-ethylhexyl 2-cyano-3, 3-diphenylacrylate; ethylhexyl p-methoxycinnamate; 3,3,5-trimethylcyclohexyl salicylate; menthyl o-aminobenzoate; 2-hydroxy-4-methoxybenzophenone; amyl p-dimethylaminobenzoate; octyl p-dimethylaminobenzoate; 2-phenylbenzimidazole-5-sulfonic acid; 5-benzoyl-4-hydroxy-2 methoxybenzene sulfonic acid; triethanolamine salicylate; 4-Tert. butyl -4-methoxy-dibenzoylmethane; and Benzalphthalide;

B. said surface active agent is selected from the group consisting of ammonium myristate, potassium oleate, triethanolamine stearate, sodium lauryl sulfate, polyoxyethylene sorbitan monolaurate and polyoxyethylene nonyl phenyl ether;

C. said water-insoluble emollient is selected from the group consisting of cetyl alcohol, oelic acid, diisopropyl adipate, polyoxypropylene (14) butyl ether, mineral oil, and dimethylpolysiloxane;

D. said volatile liquid carrier is selected from the group consisting of ethanol, isopropanol, trichlorofluoromethane, $C_{10}$–$C_{16}$ isoparaffins and cyclic dimethyl polysiloxanes;

E. said suspended particulate solid matter is selected from the group consisting of aluminumized acrylic polyester, and metallic oxides;

F. said thickening agent is selected from the group consisting of polyethylene polymer, zinc stearate, glyceryl monostearate, stearyl alcohol, paraffin wax, beeswax, fumed silica, amorphous silica, sodium magnesium silicate and colloidal magnesium aluminum silicate; and G. said liquified propellant is selected from the group consisting of butane, isobutane, propane, dimethylether, dichlorodifluoromethane, tetrafluoromethane, dichlorotetrafluoroethane, chlorodifluoromethane, chlorodifluoroethane, and difluoroethane.

5. A water-proof sunscreen composition in the form of an anhydrous oil consisting of active ultraviolet radiation absorbers comprising:

A. from about 30% to about 70% by weight of polybutene polymer having an average molecular weight of about 280 to about 750 pour point range from about −51 degrees C. to −15 degrees C.;

B. from about 2% to about 16% by weight of an active ultraviolet radiation absorber selected from the group consisting of para-aminobenzoic acid; 2-ethoxyethyl p-methoxycinnamate; diethanolamine-p-methoxycinnamate; diagalloyl trioleate; 2,2'-dihydroxy-4-methoxybenzophenone; ethyl 4-(bis(hydroxypropyl)] aminobenzoate; 2-ethylhexyl salicylate; glyceryl aminobenzoate; 2-ethylhexyl 2-cyano-3, 3-diphenylacrylate; ethylhexyl p-methoxycinnamate; 3,3,5-trimethylcyclohexyl salicylate; menthyl o-aminobenzoate; 2-hydroxy-4-methoxybenzophenone; amyl p-dimethylaminobenzoate; octyl p-dimethylaminobenzoate; 2-phenylbenzimidazole-5-sulfonic acid; 5-benzoyl-4-hydroxy-2 methoxybenzene sulfonic acid; triethanolamine salicylate; 4-Tert. butyl-4-methoxy-dibenzoylmethane; and benzalphthalide;

C. from about 35% to about 60% by weight of a volatile liquid carrier selected from the group consisting of isopropanol, $C_{12}$–$C_{14}$ isoparaffins and cyclic dimethyl polysiloxane; and D. from about 2.0% to about 15% by weight of a water-insoluble emollient selected from the group consisting of cetyl alcohol, oleic acid, diisopropyl adipate, polyoxypropylene (14) butyl ether, mineral oil, and dimethylpolysiloxane;

6. A water-proof sunscreen composition according to claim 5 wherein the polybutene polymer is a polybutene polymer having an average molecular weight of 320.

7. A water-proof sunscreen composition according to claim 5 wherein the polybutene polymer is a polybutene polymer having an average molecular weight of 460.

8. A water-proof sunscreen composition according to claim 5 wherein the polybutene polymer is a polybutene polymer having an average molecular weight of 750.

9. A water-proof sunscreen composition according to claim 5 wherein the active ultraviolet radiation absorber is Padimate O.

10. A water-proof sunscreen composition according to claim 5 wherein the active ultraviolet radiation is Oxybenzone.

11. A water-proof sunscreen composition according to claim 5 wherein the active ultraviolet radiation absorber is ethyl 4-bis[(hydroxypropyl)] aminobenzoate.

12. A water-proof sunscreen composition according to claim 5 wherein the active ultraviolet radiation absorber is ethyl p-methoxycinnamate.

13. A water-proof sunscreen composition according to claim 5 wherein the active ultraviolet radiation absorber is Padimate O and Dioxybenzone.

14. A water-proof sunscreen composition according to claim 5 wherein the volatile liquid carrier is cyclic dimethylpolysiloxane.

15. A water-proof sunscreen composition according to claim 5 wherein the volatile liquid carrier is isopropanol.

16. A water-proof sunscreen composition according to claim 5 wherein the water insoluble emollient is mineral oil.

17. A water-proof sunscreen composition according to claim 5 wherein the water insoluble emollient is dimethylpolysiloxane.

18. A water-proof sunscreen composition according to claim 5 wherein the water insoluble emollient is diisopropyl adipate.

19. A water-proof sunscreen composition in the form of anhydrous lotions and creams consisting of active ultraviolet radiation absorbers comprising:
  A. from about 30% to about 70% by weight of polybutene polymer having an average molecular weight of about 280 to about 750 pour point range from about −51 degrees C. to −15 degrees C.;
  B. from about 2% to about 16% by weight of an active ultraviolet radiation absorber selected from the group consisting of para-aminobenzoic acid; 2-ethoxyethyl p-methoxycinnamate; diethanolamine-p-methoxycinnamate; digalloyl trioleate; 2,2′-dihydroxy-4-methoxybenzophenone; ethyl 4-[bis(-hydroxypropyl)] aminobenzoate; 2-ethylhexyl salicylate; glyceryl aminobenzoate; 2-ethylhexyl 2-cyano-3, 3-diphenylacrylate; ethylhexyl p-methoxycinnamate; 3,3,5-trimethylcyclohexyl salicylate; menthy o-aminobenzoate; 2-hydroxy-4-methoxybenzophenone; amyl p-dimethylaminobenzoate; octyl p-dimethylaminobenzoate; 2-phenylbenzimidazole-5-sulfonic acid; 5-benzoyl-4-hydroxy-2 methoxybenzene sulfonic acid; triethanolamine salicylate; 4-Tert. butyl-4-methoxy-dibenzoylmethane; and benzalphthalide;
  C. from about 35% to about 60% by weight of a volatile liquid carrier selected from the group consisting of isopropanol, $C_{12}$–$C_{14}$ isoparaffins and cyclic dimethyl polysiloxane; and
  D. from about 2.0% to about 15% by weight of a water-insoluble emollient selected from the group consisting of cetyl alcohol, oleic acid, diisopropyl adipate, polyoxypropylene (14) butyl ether, mineral oil, and dimethylpolysiloxane;
  E. from about 0.5% to about 8% by weight of a thickening agent selected from the group consisting of polyethylene polymers, zinc stearate, glyceryl monostearate, stearyl alcohol, paraffin wax and beeswax.

20. A water-proof sunscreen composition in the form of an aerosol spray consisting of active ultraviolet radiation absorbers comprising:
  A. from about 10% to about 50% by weight of polybutene polymer having an average molecular weight of about 280 to about 920 and a pour point range from about −51 to about −7 degrees C.;
  B. from about 2% to about 16% by weight of an active ultraviolet radiation absorber selected from the group consisting of para-aminobenzoic acid; 2-ethoxyethyl p-methoxycinnamate; diethanolamine-p-methoxycinnamate; digalloyl trioleate; 2,2′-dihydroxy-4-methoxybenzophenone; ethyl 4-aminobenzoate; 2-ethylhexyl salicylate; glyceryl aminobenzoate; 2-ethylhexyl 2-cyano-3, 3-diphenylacrylate; ethylhexyl p-methoxycinnamate; 3,3,5-trimethylcyclohexyl salicylate; menthyl o-aminobenzoate; 2-hydroxy-4-methoxybenzophenone; amyl p-dimethylaminobenzoate; octyl p-dimethylaminobenzoate; 2-phenylbenzimidazole-5-sulfonic acid; 5-benzoyl-4-hydroxy-2 methoxybenzene sulfonic acid; triethanolamine salicylate; 4-Tert. butyl-4-methoxy-dibenzoylmethane; and benzalphthalide.
  C. from about 35% to about 60% by weight of a volatile liquid carrier selected from the group consisting of isopropanol, $C_{12}$–$C_{14}$ isoparaffins and cyclic dimethyl polysiloxane;
  D. from about 2.0% to about 15% by weight of a water-insoluble emollient selected from the group consisting of cetyl alcohol, oleic acid, diisopropyl adipate, polyoxypropylene (14) butyl ether, mineral oil, and dimethylpolysiloxane; and
  E. from about 20% to about 50% by weight of a liquified propellant selected from the group consisting of butane, isobutane, propane, dimethyl ether, dichlorodifluoromethane, tetrafluoromethane, dichlorotetrafluoroethane, chlorodifluoromethane, chlorodifluoroethane, and difluoroethane.

21. A water-proof sunscreen composition in the form of aqueous lotion and cream emulsions consisting of active ultraviolet radiation absorbers comprising:
  A. from about 5% to about 50% by weight of polybutene polymers having an average molecular weight of about 340 to 2300 and a pour point range from about −51 degrees C. to about 18 degrees C.;
  B. from about 2% to about 16% by weight of an active ultraviolet radiation absorber selected from the group consisting of para-aminobenzoic acid; 2-ethoxyethyl p-methoxycinnamate; diethanolamine-p-methoxycinnamate; digalloyl trioleate; 2,2′-dihydroxy-4-methoxybenzophenone; ethyl 4-[bis(-hydroxypropyl)] aminobenzoate; 2-ethylhexyl salicylate; glyceryl aminobenzoate; 2-ethylhexyl 2-cyano-3, 3-diphenylacrylate; ethylhexyl p-methoxycinnamate; 3,3,5-trimethylcyclohexyl salicylate; methyl o-aminobenzoate; 2-hydroxy-4-methoxybenzophenone; amyl p-dimethylaminobenzoate; octyl p-dimethylaminobenzoate; 2-phenylbenzimidazole-5-sulfonic acid; 5-benzoyl-4-hydroxy-2 methoxybenzene sulfonic acid; triethanolamine salicylate; 4-Tert. butyl-4-methoxy-dibenzoylmethane; and benzalphthalide;
  C. from about 40% to about 75% by weight of water;
  D. from about 2.0% to about 15% by weight of a water-insoluble emollient selected from the group consisting of cetyl alcohol, oleic acid, diisopropyl adipate, polyoxypropylene (14) butyl ether, mineral oil, and dimethylpolysiloxane;
  E. from about 2% to about 6% by weight of a surface active agent selected from the group consisting of ammonium myristate, potassium oleate, triethanolamine stearate, sodium lauryl sulfate, polyoxyethylene sorbitan monolaurate and polyoxyethylene nonyl phenyl ether;
  F. from about 0.5% to about 8% by weight of a thickening agent selected from the group consisting of polyethylene polymers, zinc stearate, glyceryl monostearate, stearyl alcohol, paraffin wax and beeswax; and
  G. from about 5.0% to about 15% by weight of suspended particulate solid matter selected from the group consisting of aluminumized acrylic polyester, and metallic oxides.

* * * * *